(12) United States Patent
Bright

(10) Patent No.: US 7,875,040 B2
(45) Date of Patent: Jan. 25, 2011

(54) VISUAL INDICATION OF A TRIGGER INTERMEDIATE POSITION ON AN APPLICATOR

(75) Inventor: Charles Edward Bright, Nr Burton-on-Trent (GB)

(73) Assignee: Femcare Limited (GB)

( * ) Notice: Subject to any disclaimer, the term of this patent is extended or adjusted under 35 U.S.C. 154(b) by 809 days.

(21) Appl. No.: 10/575,557

(22) PCT Filed: Oct. 15, 2004

(86) PCT No.: PCT/GB2004/004360

§ 371 (c)(1),
(2), (4) Date: Aug. 24, 2007

(87) PCT Pub. No.: WO2005/039422

PCT Pub. Date: May 6, 2005

(65) Prior Publication Data

US 2008/0109016 A1 May 8, 2008

(30) Foreign Application Priority Data

Oct. 15, 2003 (GB) ................... 0324106.4
Jul. 15, 2004 (GB) ................... 0415796.2

(51) Int. Cl.
*A61B 17/10* (2006.01)
(52) U.S. Cl. .................................... 606/142
(58) Field of Classification Search ............ 606/1, 606/104, 142, 205; 227/175.2; 604/118; 200/522
See application file for complete search history.

(56) References Cited

U.S. PATENT DOCUMENTS

| | | | | |
|---|---|---|---|---|
| 2,417,140 A | * | 3/1947 | Swanson | 604/224 |
| 2,466,714 A | * | 4/1949 | Kroeger et al. | 89/1.703 |
| 2,735,431 A | * | 2/1956 | Swanson | 604/223 |
| 3,238,941 A | * | 3/1966 | Klein et al. | 604/59 |
| 3,402,712 A | * | 9/1968 | Eisenhand | 604/61 |
| 3,777,538 A | * | 12/1973 | Weatherly et al. | 72/409.01 |
| 4,157,789 A | * | 6/1979 | Laauwe | 239/327 |
| 4,321,040 A | * | 3/1982 | Miller et al. | 433/102 |
| 4,527,724 A | * | 7/1985 | Chow et al. | 227/8 |
| 4,632,669 A | * | 12/1986 | Phipps et al. | 604/118 |
| 4,998,589 A | * | 3/1991 | Wiesendanger | 173/170 |
| 5,137,198 A | * | 8/1992 | Nobis et al. | 227/175.3 |
| 5,356,064 A | * | 10/1994 | Green et al. | 227/177.1 |
| 5,364,002 A | | 11/1994 | Green et al. | |
| 5,486,185 A | * | 1/1996 | Freitas et al. | 606/142 |
| 5,591,135 A | * | 1/1997 | Sullivan | 604/211 |
| 5,755,726 A | * | 5/1998 | Pratt et al. | 606/143 |
| 5,868,761 A | * | 2/1999 | Nicholas et al. | 606/143 |
| 5,898,400 A | * | 4/1999 | Jones et al. | 342/104 |
| 5,902,320 A | * | 5/1999 | Matsutani et al. | 606/222 |

(Continued)

FOREIGN PATENT DOCUMENTS

EP 0 630 612 12/1994

(Continued)

*Primary Examiner*—Gary Jackson
*Assistant Examiner*—Son Dang
(74) *Attorney, Agent, or Firm*—Salter & Michaelson

(57) ABSTRACT

A visual indication of an intermediate position is provided on an applicator (10) to enable an operator to correctly position the trigger (14) of the applicator to achieve a defined intermediate position.

28 Claims, 5 Drawing Sheets

U.S. PATENT DOCUMENTS

| | | | |
|---|---|---|---|
| 5,961,494 A * | 10/1999 | Hogan | 604/191 |
| 6,610,073 B1 | 8/2003 | Levinson | |
| 2003/0029451 A1* | 2/2003 | Blair et al. | 128/204.18 |
| 2005/0006433 A1* | 1/2005 | Milliman et al. | 227/176.1 |
| 2007/0093856 A1* | 4/2007 | Whitfield et al. | 606/142 |

FOREIGN PATENT DOCUMENTS

| | | |
|---|---|---|
| EP | 0 639 349 | 2/1995 |
| EP | 1 304 079 | 4/2003 |
| GB | 2 195 539 | 4/1988 |

* cited by examiner

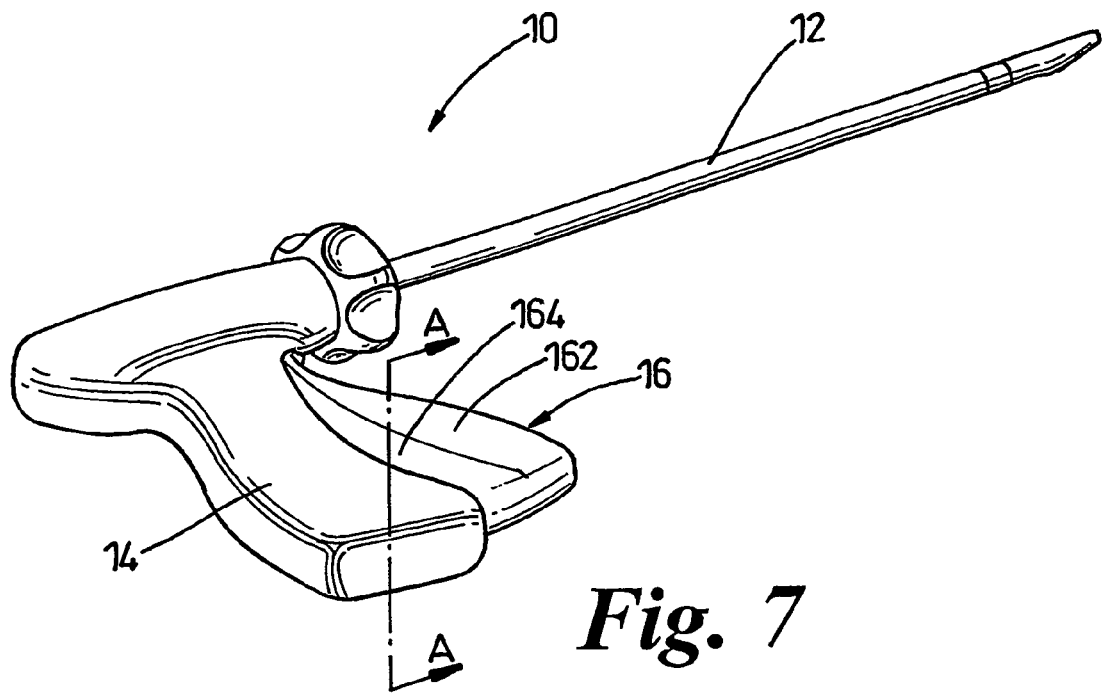
*Fig. 7*
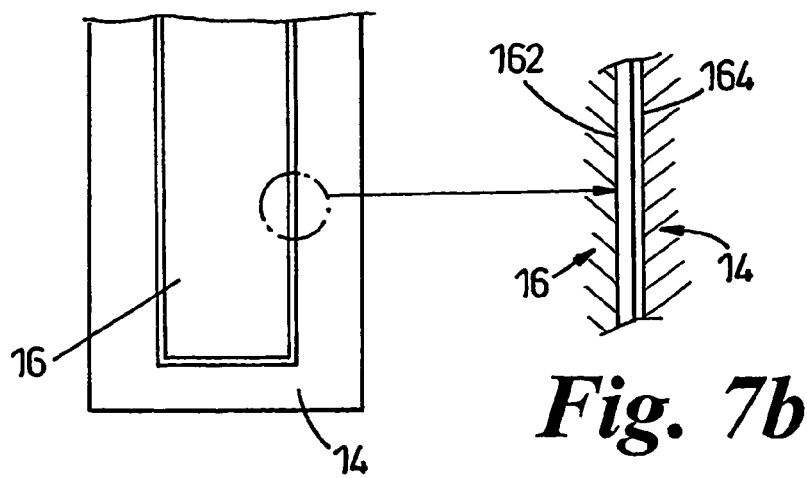
*Fig. 7a*          *Fig. 7b*

VISUAL INDICATION OF A TRIGGER INTERMEDIATE POSITION ON AN APPLICATOR

TECHNICAL FIELD

The present invention relates to applicators and more particularly to applicators for insertion and closure of surgical clips.

BACKGROUND DISCUSSION

Such clips may be for sterilisation or other medical, orthopaedic or surgical purposes where an intermediate position of an applicator or other appliance is required to be able to be accurately determined.

The term applicator is thus meant to include other appliances, particularly in the medical field, which involve a closure of a jaw or other similar gripping or squeezing action in which a specific intermediate position is required to be determined.

The present invention will now be described with reference to applicators for surgical clips. Except in open surgery it is necessary for the applicator to be inserted down a cannula for the more modern "key hole" surgery. Thus, the applicator or more precisely barrel portion of the applicator has to pass down the cannula loaded with a clip to be attached for occlusion of, for example a vas deferens or other tubular member.

With clips of the Filshie type such as disclosed in GB patent no. 2177748 excessive force applied to the clip during passage of the barrel down the cannula can result in clip failure. The clip could fall out of the barrel once it emerges from the cannula or alternatively the clip could fail by incorrect closure.

SUMMARY OF THE INVENTION

The present invention seeks to obviate this problem by providing a visual indication of an intermediate position of the applicator to ensure that there is no over-closure of a clip during passage of an applicator barrel down a cannula.

The present invention therefore provides an applicator, comprising a barrel portion and a handle portion attached thereto, the barrel portion comprising means for holding a surgical clip and the handle comprising trigger means, the trigger means being operative to effect closure of a surgical clip held within the barrel by movement of the trigger from a first position to a second position at which second position the applicator is operative to effect closure of the clip, and in which the trigger is provided with a visual indicator means indicative of an intermediate trigger position, at which intermediate position the surgical clip held in the barrel is closed to a half closed position.

Preferably the visual indication comprises an indentation on said trigger.

Alternatively the visual indication comprises a reduced section of the trigger.

In a further embodiment the visual indication comprises groove means in the trigger.

In a further embodiment the groove means may comprise means for engaging with a removable stop means, the removable stop means being co-operative with a portion of the handle to prevent movement of the trigger past a predetermined position.

Preferably the groove means is present on both sides of said trigger.

Preferably the stop means may comprise a U shaped member which is designed in a first locking position to sit within the groove means and to protrude from the groove means to form the stop means.

Preferably the U shaped member comprises spring steel or similar material ensuring secure engagement with the groove means.

Preferably the U shaped member comprises means for gripping by a surgeon to effect removal of the U shaped member from the trigger, enabling movement of the trigger past the predetermined position.

In a further embodiment the trigger may comprise two or more colours arranged to identify specific portions of the trigger.

In a further embodiment the handle includes a recess, the trigger being pivotally mounted within the handle, the trigger being movable into the recess when the trigger is operated, and in which the trigger is dimensioned to have minimal clearance between itself and the recess over substantially the whole pivotal movement of the trigger.

Preferably the visual indicator means is provided by a change of surface texture at a defined position across the trigger.

This change of surface texture will provide a visual indication of the defined position without any substantial variation of the surface dimension of the trigger.

The advantage of this design feature is that as the trigger is moved into and out of the handle there will be no appreciable gap between the trigger and the recess of the handle.

In surgical operation surgical gloves are worn and if there is any substantial gap between the trigger and the recess as the trigger is operated then there is a possibility of a glove catching between the trigger and the recess and being torn. This would create hygienic problems were it to occur and thus this feature is an important advantage of this embodiment.

The visual indication feature is further enhanced by the pressure felt by the surgeon on the trigger as the clip is partially closed.

The present invention also provides an applicator comprising a handle portion and a barrel portion, the barrel portion having gripping means at a distal end from the handle portion for gripping an object in which the handle portion includes trigger means operative to move into and out of a main body portion of the handle and being operative to move the gripping means to grip an object and in which the trigger means is provided with visual indication means indicating a defined intermediate position of the trigger means, the unusual indicator comprising a change in surface texture at an defined intermediate position the surface texture change being dimensioned such that the clearance between the trigger means and the main body portion is minimal, thereby removing the possibility of snagging surgical gloves on movement of the trigger.

DESCRIPTION OF THE DRAWINGS

Embodiments of the present invention will now be described by reference to the accompanying drawings in which:

FIG. 7 shows a further embodiment of the application according to the present invention in perspective view, FIGS. 7a and 7b showing a portion of the trigger and main body portion of the handle in cross section with an enlarged portion illustrating the change in texture feature.

DETAILED DESCRIPTION

Figure 1:
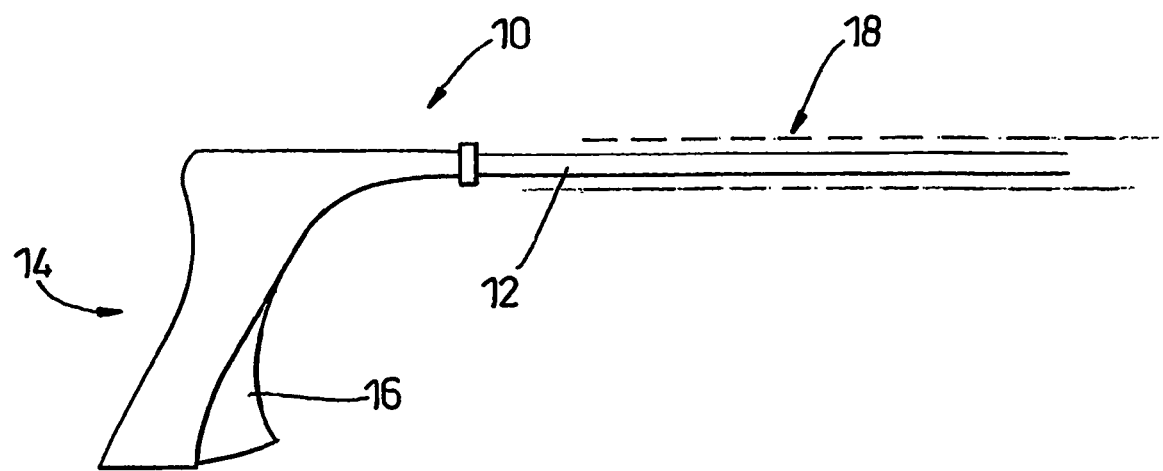
FIG. 1 shows an applicator for clips of the Filshie type.

With reference now to the drawings an applicator 10 for applying clips of the Filshie type (as described in European patent application no. 03075212.5) is shown. Such clips are of the hinged type and will be hereinafter referred to as Filshie clips.

The applicator 10 comprises a barrel portion 12 and a handle portion 14 including a trigger 16.

The applicator is designed to pass down a relatively small diameter cannula 18.

In order to do so it is necessary for the Filshie clip to pass down the cannula whilst in position in the applicator at the end of barrel 12. For a more detailed description reference is made to PCT application no.

A problem which arises is that if the clip is closed too far by application of trigger 16 then the clip may partially latch and the clip will not subsequently be able to be correctly attached.

Figure 2:
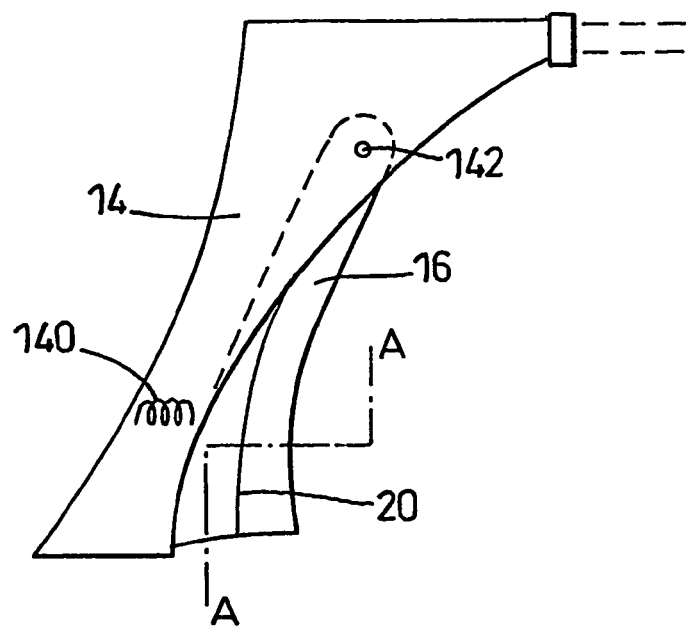
FIG. 2 shown in greater detail the operating handle of the applicator of FIG. 1 in accordance with the present invention.

To enable the surgeon to ascertain the correct position of the trigger to achieve the half closed position the trigger and handle combination is provided with visual indication means 20 as indicated in FIG. 2.

This visual indication means preferably comprises an elongate linear feature easily discernible by a surgeon enabling the surgeon to readily set the trigger to a correct position.

The visual indicator may also comprise means for physically preventing further movement of the trigger past the correct semi-closed position of the clip this being illustrated hereinafter with reference to FIGS. 4, 5 and 6.

With reference to FIG. 2 the visual indicator 20 marks a position at which with trigger 16 is moved on pivot 142 against for example return spring 140 the clip positioned at the distal end of barrel 12 will be in a semi-closed position.

Preferably the visual indicator line 20 will exist for a substantial distance over the trigger to provide a visual indication even when the trigger is being gripped by one or more of the digits of a surgeons hand.

In FIG. 2 a section of the trigger along line A-A is shown for various embodiments illustrated in FIGS. 3 to 6.

Figure 3:
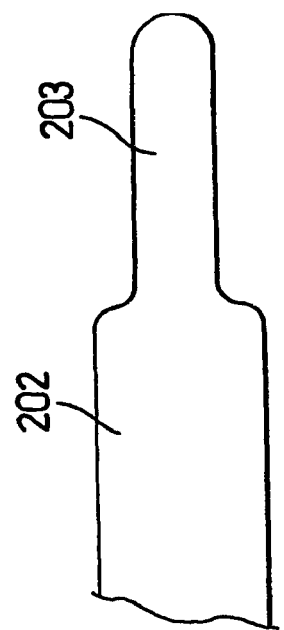
FIG. 3 shows a first embodiment of the visual indication means according to the present invention.

In FIG. 3 the trigger 14 is provided with a dual thickness shape shown at 202,203 the change in thickness providing the visual indication 20.

Figure 4A:
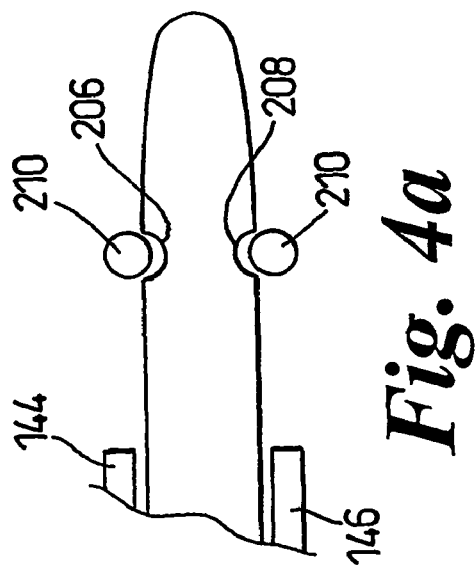
FIGS. 4a and 4b show a second embodiment with the trigger in two positions.
Figure 4B:
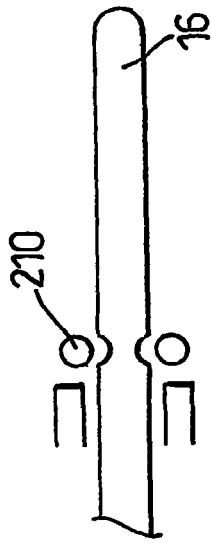

In FIGS. 4a and 4b a groove 206, 208 is provided, preferably on both sides of the trigger.

The groove can provide the visual indication itself but in a specific embodiment a U shaped member 210 (see FIGS. 5 and 6) is inserted along the groove.

For illustrative purposes an edge portion 144, 146 of handle 14 is shown illustrating that when trigger 16 is pulled back the U shaped member 210 abuts the edges 144, 146 and physically prevents further movement of the trigger.

Figure 5:
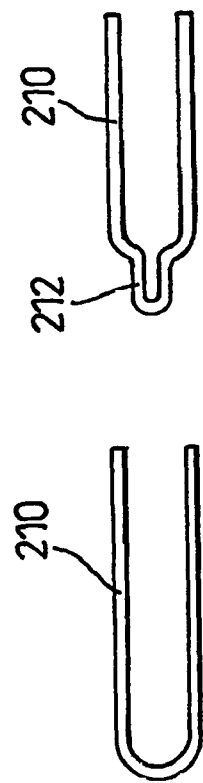
FIG. 5 shows a first embodiment of the U shaped member comprising the stop means.

The U shaped member 210 is shown in a first embodiment in FIG. 5 and preferably comprises a spring steel member allowing it to grip the grooves in trigger 16. Alternatively a suitable rigid plastic material may be used.

Figure 6:
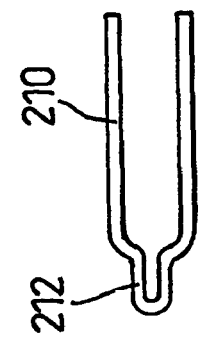
FIG. 6 shows a second embodiment of the U shaped member comprising said stop means.

In FIG. 6 the U shaped member is provided with gripping means 212 facilitating easy removal once capable closure of the Filshie clip is required.

The visual indication 20 may also be provided or enhanced by a change in colour of the trigger along line 20.

With reference now to FIG. 7 in an alternative embodiment the trigger 16 comprises two separate surface features.

One part 162 (which could be the forward part on the rearward part) is provided with a surface texture whilst the other part 164 is a different surface texture which could for example be smooth. The advantage of this embodiment is that the trigger can be moulded from a single, preferably plastics, injection without use of a colouring agent in part of the trigger and also because the texturing can be made to raise or lower the surface by only a very small amount, possibly a few microns, the trigger can be made to slide into and out of the recess 1420 (shown exploded in FIG. 9) with minimal clearance. This is shown clearly in FIGS. 7a and 7b, FIG. 7a showing a cross section through a portion of the handle 14 and trigger 16 and FIG. 7b showing a magnified view of a section of the trigger 16 showing the edges surfaces 162 and 164 and illustrating the minimal change in surface dimension.

This removes the possibility of snagging or catching the surgical gloves of a surgeon whilst operating the applicator.

Additionally the amount of textured (or untextured) trigger left exposed as the trigger is pressed allows the surgeon a first appraisal of the level of clip closure and, as explained with reference to FIG. 8 the applicator trigger will increasingly provide a feedback pressure as a clip is squeezed to a half closed position. Thus the surgeon can feel the clip pressure and look at the position of the textured line in the handle to provide visual and tactile approval of the position of the clip.

Figure 8:
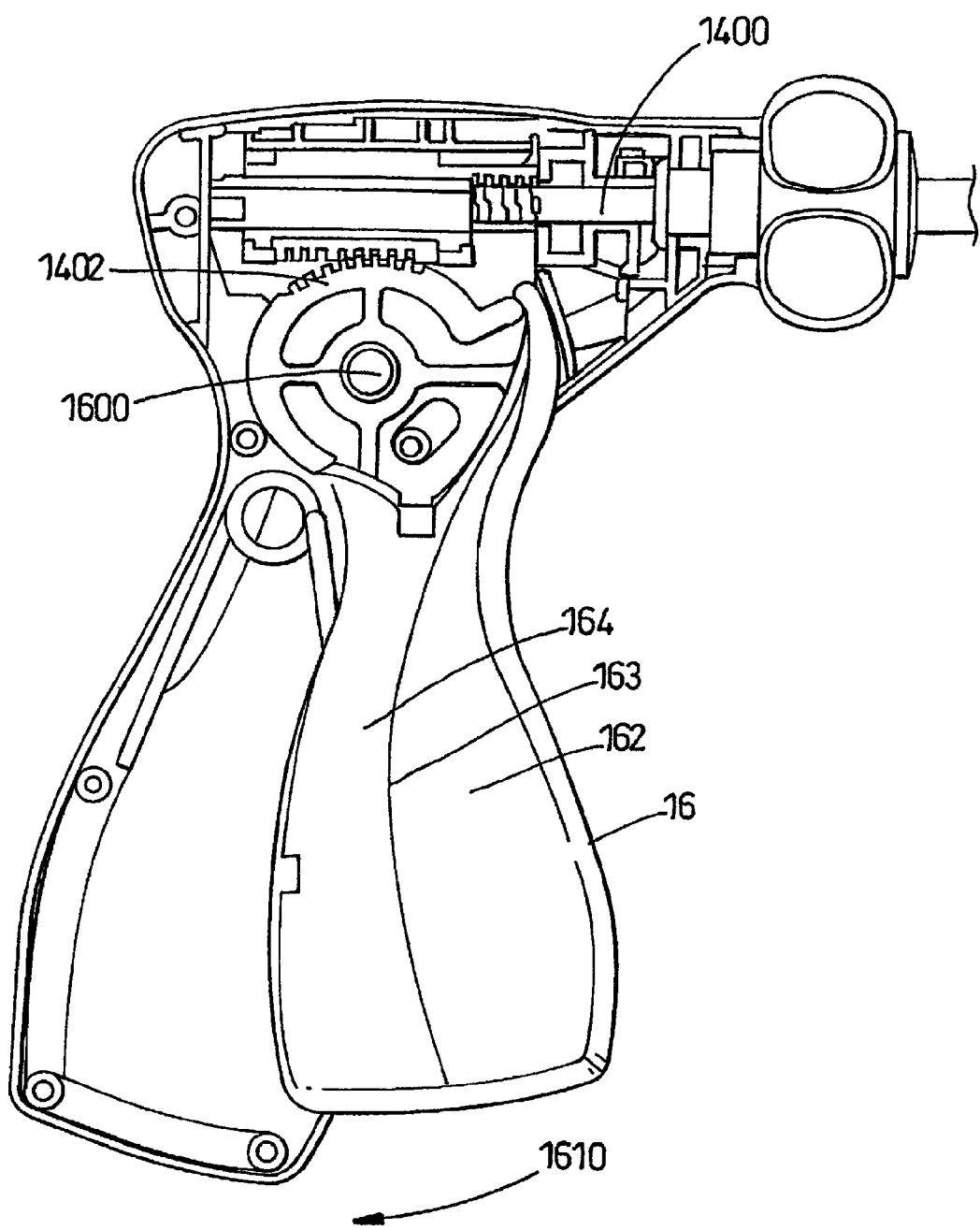
FIG. 8 shows a partial cross section of the applicator of FIG. 7 illustrating the operation of the trigger and, FIG. 9 shows an exploded view of the applicator of FIG. 7.

In FIG. 8 the trigger 16 is movable on a pivot 1600 and drives the clip closure mechanism 1400 via a rack and pinion drive 1402.

As the trigger 16 moves in the direction of arrow 1610 to close the clip a feedback pressure is felt on the trigger 16 by the surgeon combining with the position of texture change line 163 to provide the surgeon with a tactile as well as visual indication.

Figure 9:
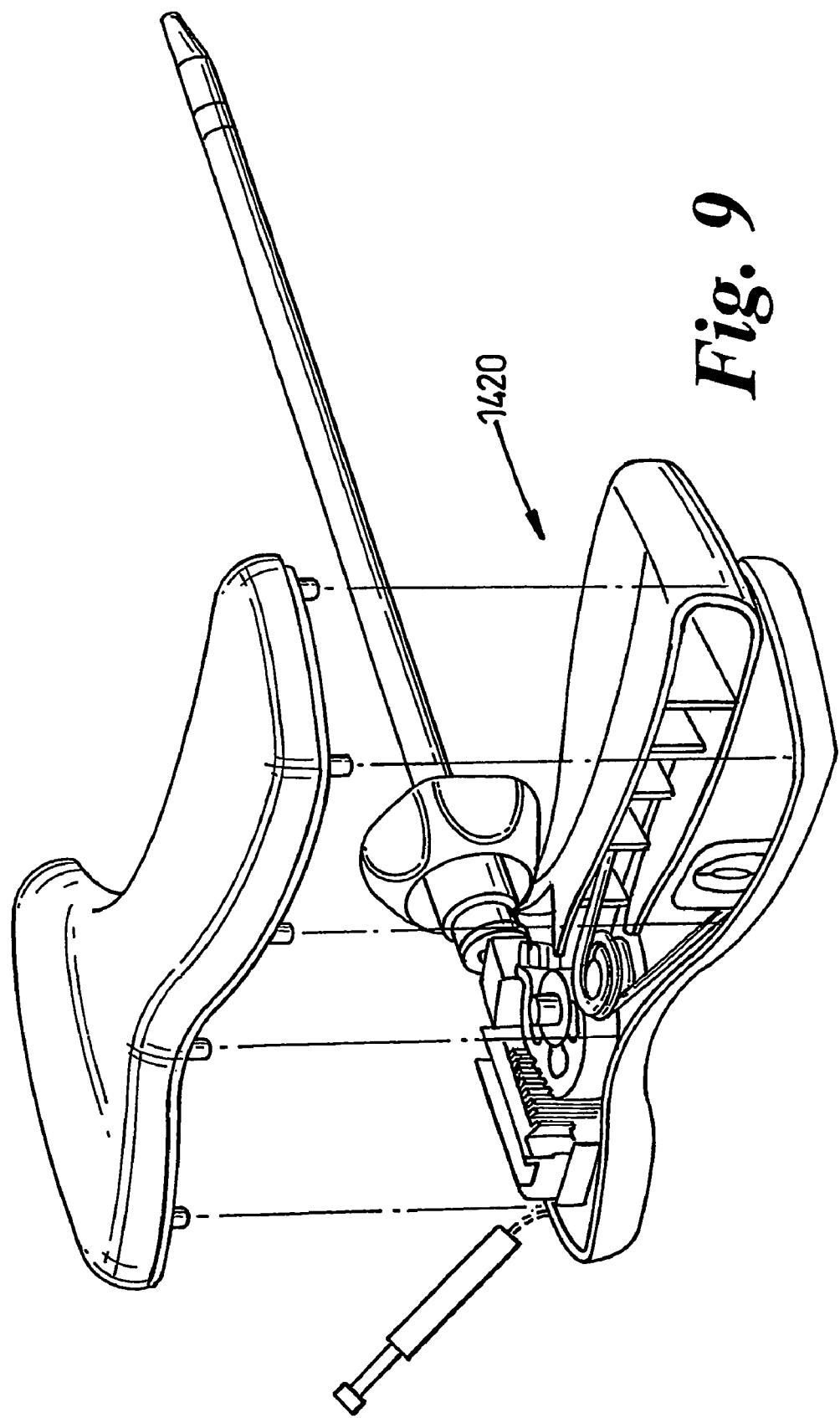

FIG. 9 shows the applicator in an exploded form to provide a further explanation of the embodiment of FIG. 7.

The invention claimed is:

1. An applicator comprising a barrel portion and a handle portion attached to the barrel portion, said barrel portion comprising means for holding a surgical clip and said handle portion comprising trigger means, said trigger means being operative to effect closure of a surgical clip held within said barrel portion by movement of said trigger means from a first position to a second position, at which second position said applicator is operative to effect closure of said clip, and in which said trigger means is provided with a visual indicator means indicative of an intermediate trigger position, at which intermediate position said surgical clip held in said barrel portion is closed to a part closed position, said visual indicator means defining an elongate visual indicator line that extends a substantial distance over the trigger means to provide a visual indication even when the trigger means is being gripped by one or more of the digits of a users hand, said visual indicator line extending in a direction between a pivot of the handle and a base end of the trigger.

2. An applicator as claimed in claim 1, in which said visual indicator means comprises an indentation on said trigger means.

3. An applicator as claimed in claim 1, in which said visual indicator means comprises a reduced section of said trigger means.

4. An applicator as claimed in claim 1, in which said visual indicator means comprises groove means in said trigger means.

5. An applicator as claimed in claim 4, in which said groove means comprises means for engaging with a removable stop means, said removable stop means being co-operative with a portion of said handle portion to prevent movement of said trigger means past a predetermined position.

6. An applicator as claimed in claim 5, in which said groove means is present on both sides of said trigger means.

7. An applicator as claimed in claim 6, in which said stop means comprises a U shaped member which is designed in a first locking position to sit within said groove means and to protrude from said groove means to form said stop means.

8. An applicator as claimed in claim 7, in which said U shaped member comprises spring steel or similar material ensuring secure engagement with said groove means.

9. An applicator as claimed in claim 8, in which said U shaped member comprises means for gripping by a surgeon to effect removal of said U shaped member from said trigger means enabling movement of said trigger means past said predetermined position.

10. An applicator as claimed in claim 1, in which the trigger means comprises two or more colors arranged to identify a specific position of the trigger means.

11. An applicator as claimed in claim 1 in which the handle portion includes a recess, the trigger means being pivotally mounted within said handle portion to be moveable within said recess when said trigger means is operated and in which the trigger means is dimensioned to have minimal clearance between itself and the recess edges over substantially the whole pivotal movement of the trigger means.

12. An applicator as claimed in claim 11 in which the visual indicator means is provided by a change in surface texture at a defined position across the trigger means.

13. An applicator as claimed in claim 12 in which trigger means provides a feedback pressure as a clip is being moved from an open to a half closed position this feedback pressure providing a tactile sense to the surgeon which when combined with the visual indication provides additional information on the position of the clip.

14. An applicator comprising a handle portion and a barrel portion, said barrel portion having gripping means at a distal end from said handle portion for gripping an object in which said handle portion include a trigger operative to move into and out of a main body portion of said handle portion and being operative to move said gripping means to grip an object and in which said trigger is provided with a visual indicator line that extends a substantial distance over the trigger indicating a defined intermediate position of said trigger, said visual indicator line defined by a change in surface texture at a defined intermediate position, said surface texture change being dimensioned such that the clearance between the trigger and said main body portion is minimal, thereby removing the possibility of snagging surgical gloves on movement of the trigger, said visual indicator line extending in a direction between a pivot of the handle and a base end of the trigger.

15. A medical appliance comprising: a barrel portion; a handle portion; said barrel portion including a holder for a surgical clip; said handle portion including a trigger that is operative to effect closure of the surgical clip from a first position to a second position; said trigger in said second position effecting full closure of the surgical clip; said trigger having a visual indicator defined by an elongate visual indicator line that extends a substantial distance over a visual surface of the trigger and that is representative of an intermediate trigger position between said first and second positions; said trigger at said intermediate position maintaining said surgical clip at a partially closed position, said handle portion includes a recess, the trigger being pivotally mounted within the handle portion to extend through said recess for access by a surgeon, said visual indicator line extending in a direction between a pivot of the handle and a base end of the trigger.

16. A medical appliance as claimed in claim 15, in which said visual indicator comprises an indentation on said trigger.

17. A medical appliance as claimed in claim 15, in which said visual indicator comprises a reduced section of said trigger.

18. A medical appliance as claimed in claim 15, in which said visual indicator comprises a groove in said trigger.

19. A medical appliance as claimed in claim 15, in which said visual indicator is defined by two or more colors arranged to identify a specific position of the trigger.

20. A medical appliance as claimed in claim 15, in which the trigger is dimensioned to have a minimal clearance with an edge defining the recess.

21. A medical appliance as claimed in claim 15 wherein the trigger provides a visual indication even when the trigger is being gripped by one or more of the digits of a users hand.

22. A medical appliance as claimed in claim 15 wherein said visual indicator line is defined by a change in thickness of the trigger.

23. A medical appliance comprising:
a barrel;
a handle;
said barrel including a distal holder for a surgical clip;
said handle including a trigger that is operative to effect closure of the surgical clip from a first position to a second position;
said trigger in said second position effecting full closure of the surgical clip;
said trigger having a visual indicator line that extends over a visual surface of the trigger and that is illustrative of an intermediate trigger position between said first and second positions;
said trigger at said intermediate position maintaining said surgical clip at a partially closed position;
said handle includes an elongated recess;
said trigger being pivotally mounted within the handle to be movable within the recess when the trigger is operated;
and an elongated removable stop member that is selectively engageable with said visual indicator line and co-operative with an outer surface of said handle to prevent movement of said trigger past a predetermined position;
and wherein the visual indicator line extends a substantial distance over the visual surface of the trigger and extends in a direction between a pivot of the handle and a base end of the trigger.

24. A medical appliance as claimed in claim 23 wherein the visual indicator line is defined by at least one elongated groove for receiving the elongated removable stop member.

25. A medical appliance as claimed in claim 24 including a pair of elongated grooves on respective opposed sides of the trigger.

26. A medical appliance comprising:
a barrel;
a handle;
said barrel including a distal holder for a surgical clip;
said handle including a trigger that is operative to effect closure of the surgical clip from a first position to a second position;
said trigger in said second position effecting full closure of the surgical clip;
said trigger having a visual indicator line that extends over a visual surface of the trigger and that is illustrative of an intermediate trigger position between said first and second positions;
said trigger at said intermediate position maintaining said surgical clip at a partially closed position;
said handle includes an elongated recess;
said trigger being pivotally mounted within the handle to be movable within the recess when the trigger is operated;
and an elongated removable stop member that is selectively engageable with said visual indicator line and co-operative with an outer surface of said handle to prevent movement of said trigger past a predetermined position;
wherein the visual indicator line is defined by a pair of elongated grooves on respective opposed sides of the trigger for receiving the elongated removable stop member;
and wherein the elongated removable stop member comprises a U-shaped member having legs that are engaged in respective grooves, said U-shaped member including means for gripping by a user to effect removal of said U-shaped member from said trigger to enable movement of said trigger past said predetermined position.

27. A medical appliance as claimed in claim 23 wherein the visual indicator line is defined by groove means for receiving the elongated removable stop member, said elongated removable stop member having an engaged position that enables movement of said trigger but prevents movement of said trigger past said predetermined position, and a removed position that enables the trigger to move past said predetermined position.

28. A medical appliance comprising:
a barrel;
a handle;
said barrel including a distal holder for a surgical clip;
said handle including a trigger that is operative to effect closure of the surgical clip from a first position to a second position;
said trigger in said second position effecting full closure of the surgical clip;
said trigger having a visual indicator line that extends over a visual surface of the trigger and that is illustrative of an intermediate trigger position between said first and second positions;
said trigger at said intermediate position maintaining said surgical clip at a partially closed position;
said handle includes an elongated recess;
said trigger being pivotally mounted within the handle to be movable within the recess when the trigger is operated;
and an elongated removable stop member that is selectively engageable with said visual indicator line and co-operative with an outer surface of said handle to prevent movement of said trigger past a predetermined position;
and wherein the visual indicator line extends in a direction between a pivot of the handle and a base end of the trigger, and the indicator line is visualized in comparison to a handle elongated surface defined about the elongated recess, the remaining visual length of indicator line being a measure of the degree of depression of the trigger, and correspondingly the degree of closure at the surgical clip.

\* \* \* \* \*